United States Patent
Kobayashi et al.

(10) Patent No.: US 10,499,966 B2
(45) Date of Patent: Dec. 10, 2019

(54) BONE FIXATION SYSTEM INCLUDING AN IMPLANT HAVING A PLATE PORTION AND A MESH PORTION

(71) Applicant: DePuy Synthes Products, Inc., Raynham, MA (US)

(72) Inventors: Kenneth Kobayashi, Exton, PA (US); Harry Thomas Hall, IV, Chester Springs, PA (US); Glen Pierson, Glenmoore, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 228 days.

(21) Appl. No.: 15/791,958

(22) Filed: Oct. 24, 2017

(65) Prior Publication Data

US 2019/0117283 A1   Apr. 25, 2019

(51) Int. Cl.
*A61B 17/80* (2006.01)
*A61B 17/86* (2006.01)
*A61B 17/56* (2006.01)

(52) U.S. Cl.
CPC ...... *A61B 17/8085* (2013.01); *A61B 17/8014* (2013.01); *A61B 17/8057* (2013.01); *A61B 17/8061* (2013.01); *A61B 17/8605* (2013.01); *A61B 17/8625* (2013.01); *A61B 2017/564* (2013.01)

(58) Field of Classification Search
CPC ............ A61B 17/8085; A61B 17/8014; A61B 17/8057; A61B 17/8071
See application file for complete search history.

(56) References Cited

U.S. PATENT DOCUMENTS

| | | | |
|---|---|---|---|
| 5,139,497 A | 8/1992 | Tilghman et al. | |
| 5,139,528 A | 8/1992 | Koch et al. | |
| 5,743,913 A | 4/1998 | Wellisz | |
| 6,391,059 B1 | 5/2002 | Lemperle et al. | |
| 6,620,332 B2 | 9/2003 | Amrich | |
| 6,652,530 B2 | 11/2003 | Ip et al. | |
| 7,018,418 B2 | 3/2006 | Amrich et al. | |
| 7,335,204 B2 | 2/2008 | Tornier | |
| 8,147,493 B2 | 4/2012 | Dutoit et al. | |
| 8,764,809 B2 | 7/2014 | Lorenz et al. | |
| 8,940,027 B2 | 1/2015 | Williams | |
| 9,023,085 B2 | 5/2015 | Strippgen | |
| 9,526,528 B2 | 12/2016 | Sutterlin, III | |
| 2002/0173848 A1 | 11/2002 | Sachs | |
| 2002/0173854 A1* | 11/2002 | Amrich ............. A61B 17/8085 623/23.53 |

* cited by examiner

Primary Examiner — Christian A Sevilla
(74) Attorney, Agent, or Firm — BakerHostetler

(57) ABSTRACT

A bone fixation system is configured to be implanted and secured to a bone so as to stabilize a bone. The bone fixation system includes an implant having a plate portion configured to be secured to a first segment of the bone by a first bone anchor, and a second segment of the bone by a second one anchor. The implant further includes a mesh portion configured to abut a third segment of the bone to prevent movement of the third segment relative to both the first segment and the second segment. The implant defining an outer perimeter defined in part by the plate portion and in part by the mesh portion.

19 Claims, 7 Drawing Sheets

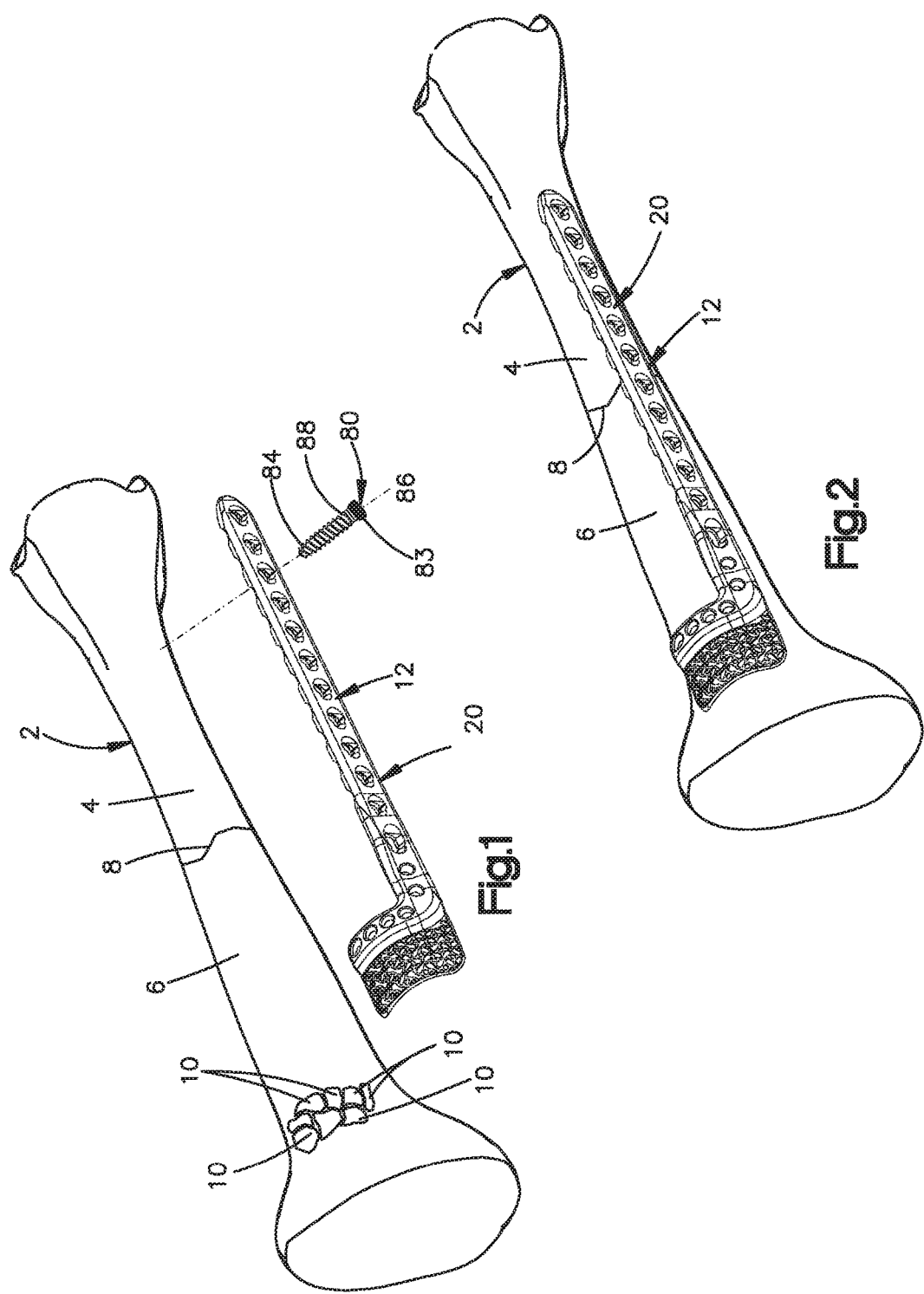

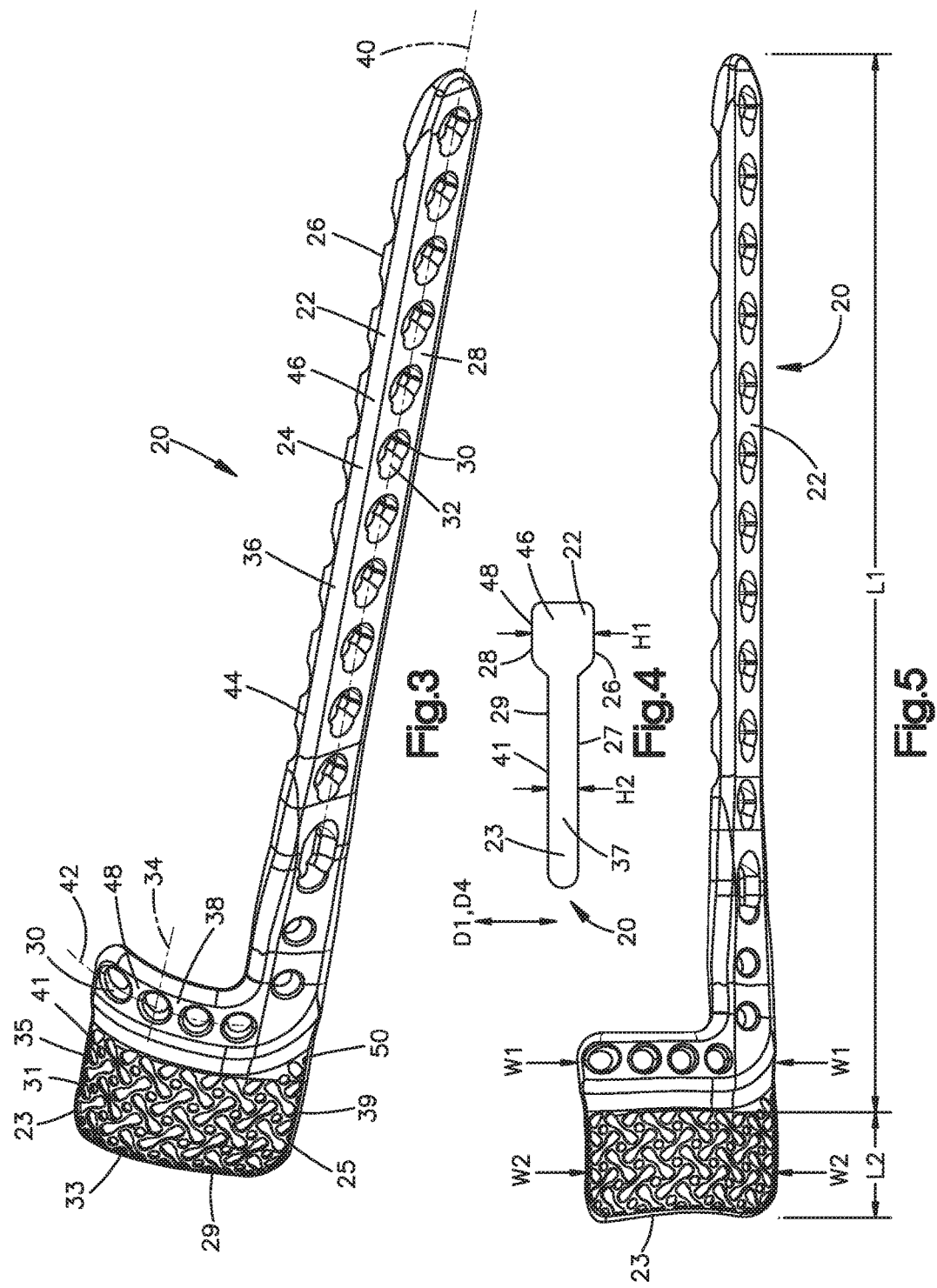

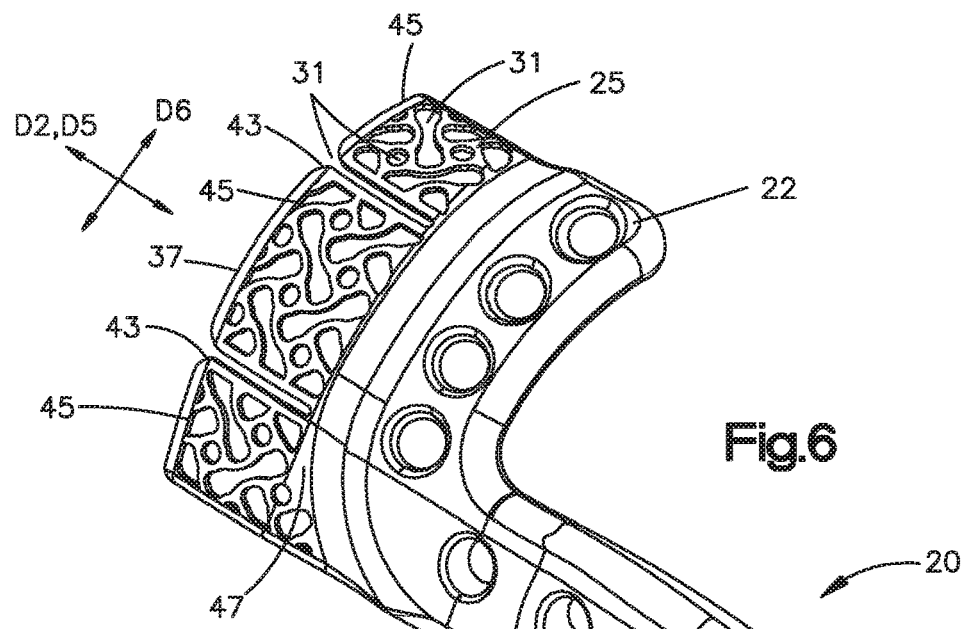
Fig.6
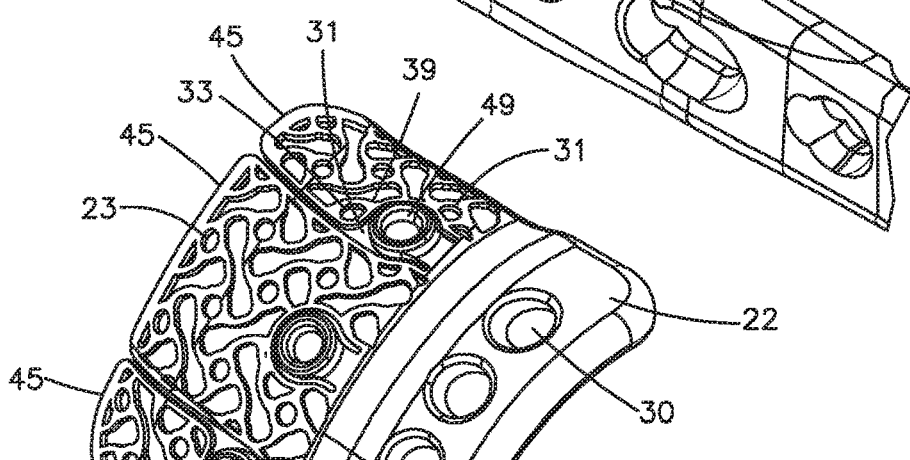
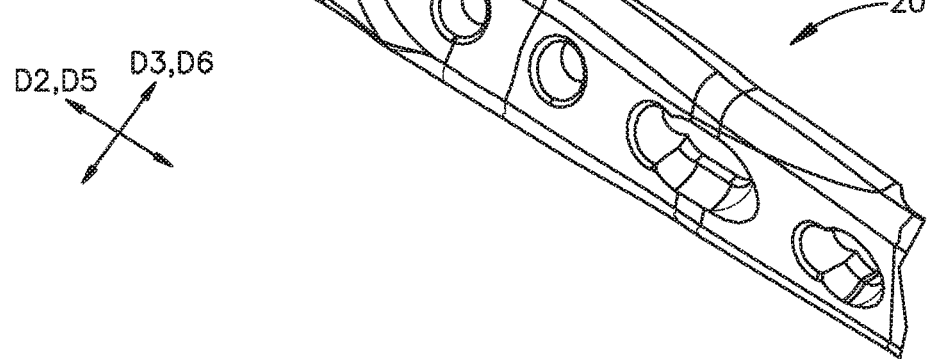
Fig.7

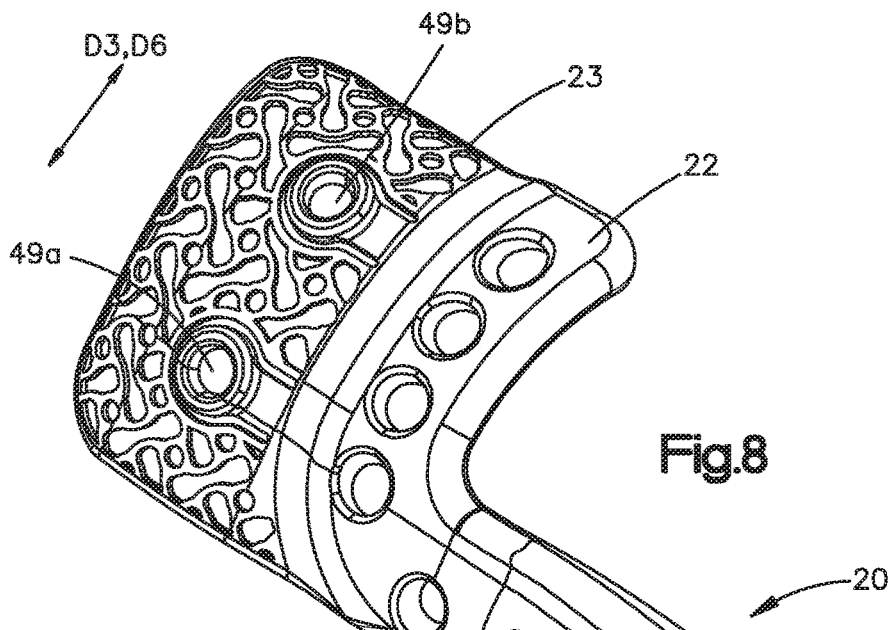
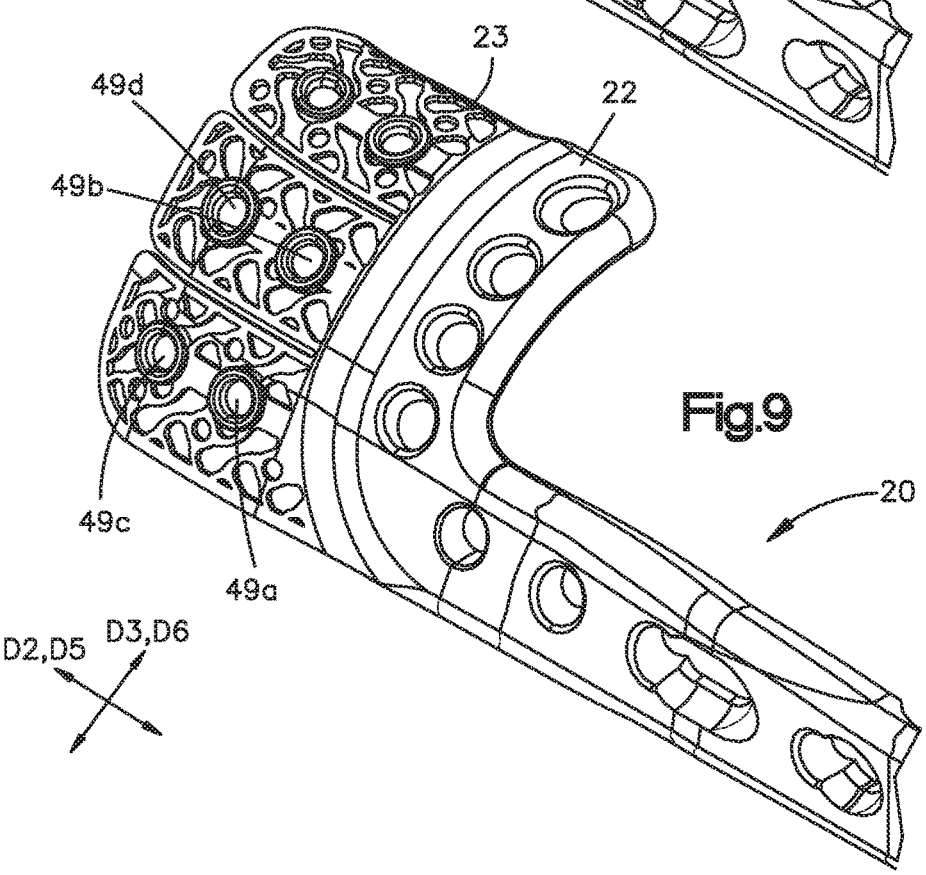

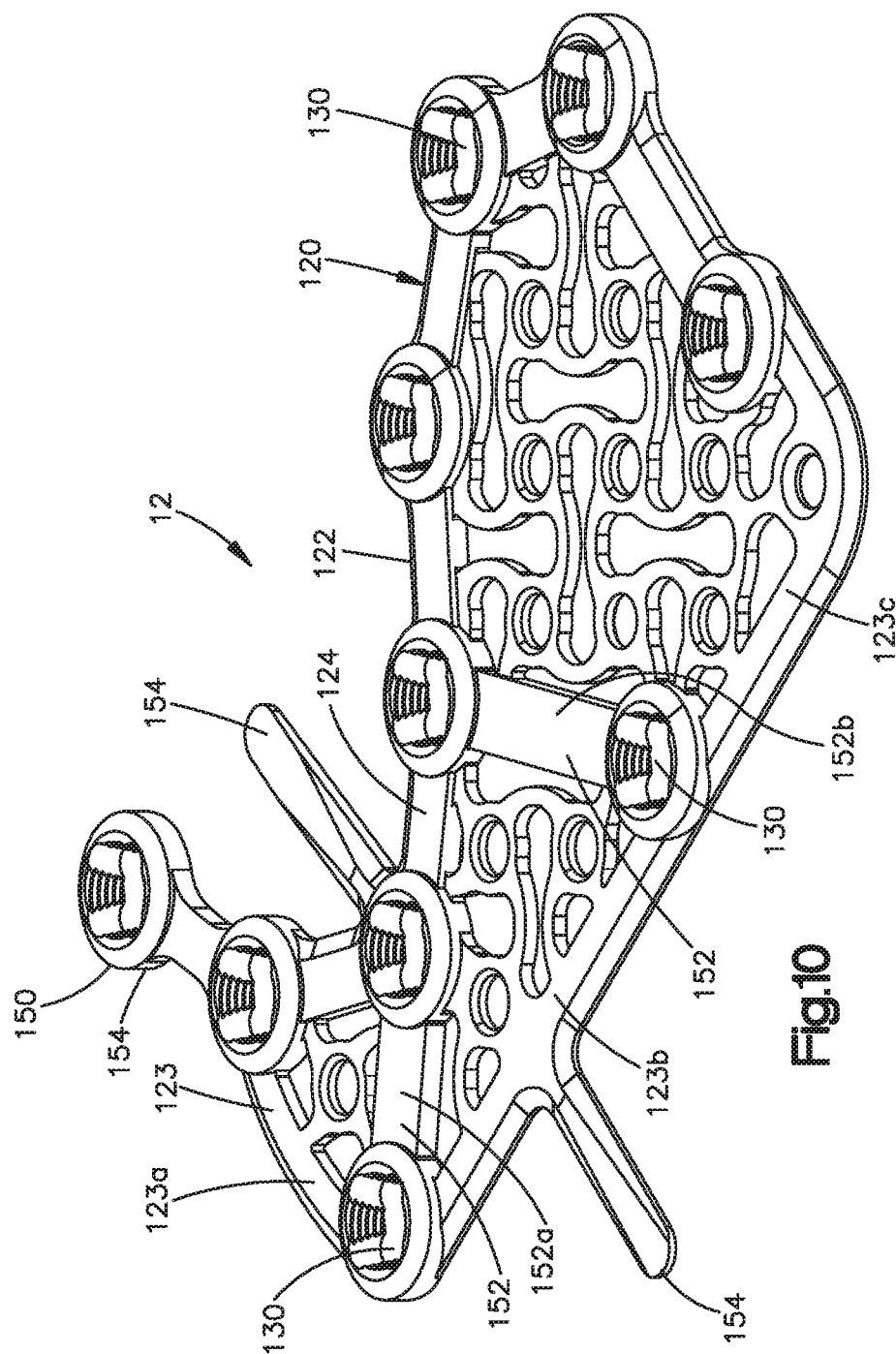

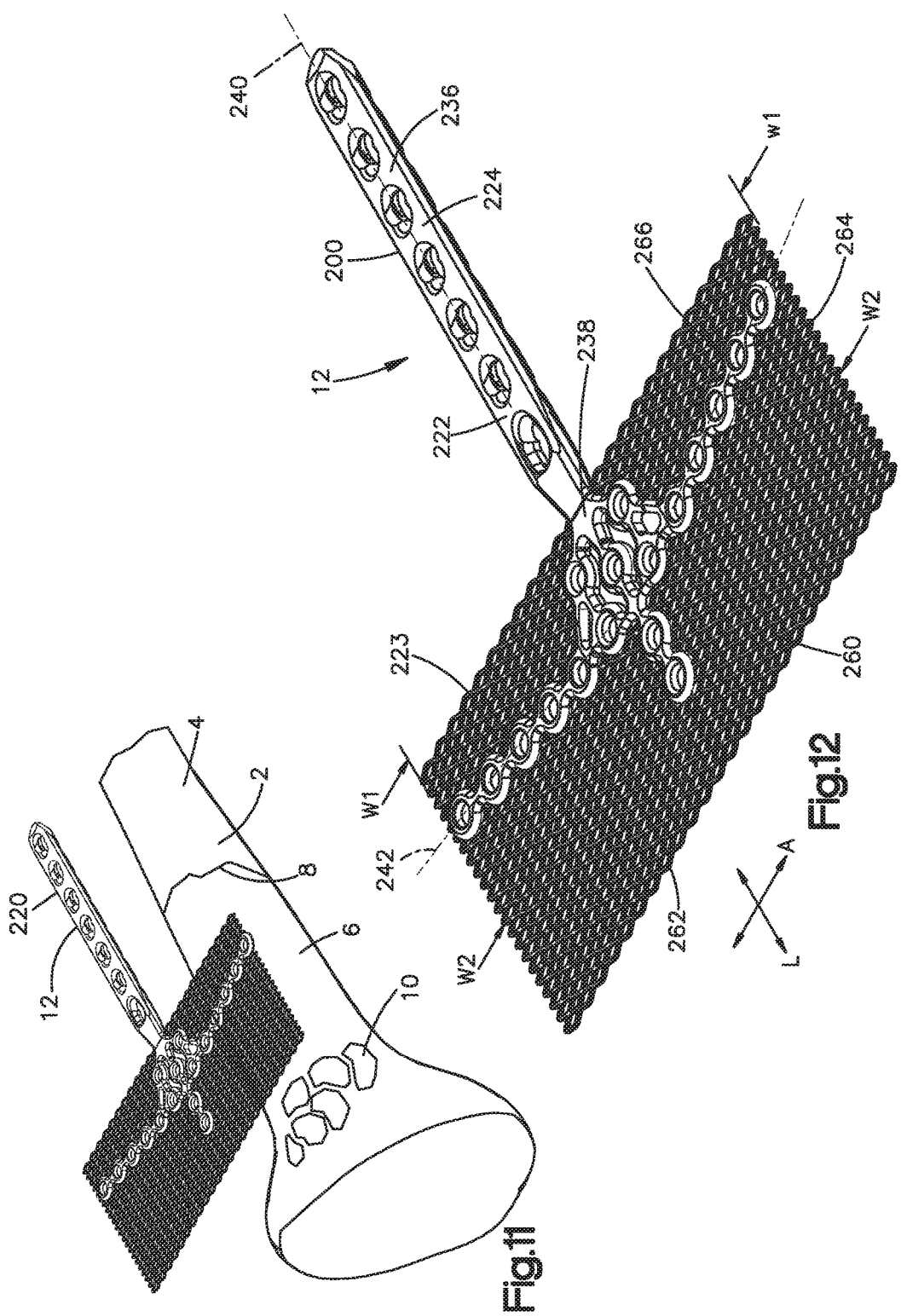

BONE FIXATION SYSTEM INCLUDING AN IMPLANT HAVING A PLATE PORTION AND A MESH PORTION

TECHNICAL FIELD

This disclosure relates generally to bone fixation, and in particular relates to a bone fixation system provides compression to enhance the stabilization of bone fractures.

BACKGROUND

Many types of bone fixation systems are conventionally available to stabilize bone fragments following bone fractures to promote bone healing. Bone fixation systems typically include a bone plate that is placed against the bone across the fracture location. Bone anchors, typically configured as bone screws, are driven through bone fixation holes of the bone plate and into the respective underlying bone fragments. The bone fragments are thus stabilized with respect to the bone plate and each other. The bone fragments can be compressed toward each other prior to reduce the fracture prior to fixation of the bone anchors.

Bone screws are conventionally available as locking screws or non-locking screws (also known as compression screws). Locking screws are configured to lock to the bone plate. For instance, locking screws typically can be externally threaded at the screw head, and the bone plate typically includes threading in the fixation hole. The locking screw is inserted through the fixation hole of the bone plate, and rotated to gain purchase with the underlying bone as it is driven into the bone. The locking screw is rotated until the screw head is inserted into the fixation hole, at which point the threading of the screw head purchases with the threading in the fixation hole. Thus, the locking screw is locked to the bone plate, thereby creating a fixed angle construct and preventing back out of the bone screw.

Alternatively, the bone screws can be configured to compress the bone plate against the underlying bone. In particular, the external surface of the bone screw can be unthreaded. Accordingly, the bone screw is driven into the underlying bone until the screw head bears against the bone plate (typically in the fixation hole). Continued rotation of the bone screw causes the screw head to compress the bone plate against the underlying bone. This can be useful when it is desired to compress two or more bone fragments against each other to promote bone healing. Unfortunately, conventional locking screws are not also configured to cause compression of the bone plate against the underlying bone.

Unfortunately, many high-energy fractures produce highly comminuted fractures that are not easily addressed with conventional bone plating techniques. Intra-articular and juxta-articular fractures typically result in highly comminuted fractures. In particular, the small bone fragments associated with highly comminuted fractures are too small to receive bone screws. As a result, these bone fragments are often left untreated.

It is therefore desirable to provide a bone plate that is configured to stabilize highly comminuted bone fractures.

SUMMARY

The following Summary is provided to introduce a selection of concepts in a simplified form that are further described below in the Detailed Description of Illustrative Embodiments. This Summary is not intended to identify key features or essential features of the invention, nor is it intended to be used to limit the scope of the invention. Reference is made to the claims for that purpose.

In accordance with an aspect of the disclosure, the application discloses an implant including a plate portion and a mesh portion, wherein the implant defines an outer perimeter defined at least partially by the plate portion and further defined at least partially by the mesh portion.

In accordance with an aspect of the disclosure, the application discloses a method of stabilizing a bone, the bone including a first bone fragment, a second bone fragment, a third bone fragment, a first defect between the first bone fragment and the second bone fragment, and a second defect between the second bone fragment and the third bone fragment. The method includes the step of moving an implant toward the bone, the implant includes a plate portion, a mesh portion, and an outer perimeter defined in part by the plate portion and in part by the mesh portion. The method further includes the step of inserting a bone anchor through a first bone fixation hole defined by the plate portion, and into the first bone segment, inserting a second bone anchor through a second bone fixation hole defined by the plate portion, and into the second bone segment, and abutting the mesh portion with the third bone segment.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 1 is an exploded perspective view of a bone fixation system according to one aspect of the disclosure, the bone fixation system including an implant and a bone fixation member configured to attach the implant to an underlying fractured bone;

FIG. 2 is a perspective view of the bone fixation system illustrated in FIG. 1, showing the implant attached to the underlying fractured bone;

FIG. 3 is a perspective view of the implant illustrated in FIG. 1 according to one embodiment, the implant including a plate portion and a mesh portion;

FIG. 4 is a side elevation view of the implant illustrated in FIG. 1;

FIG. 5 is a top plan view of the implant illustrated in FIG. 1 according to another embodiment, the implant including a plate portion and a mesh portion;

FIG. 6 is a perspective view of the implant illustrated in FIG. 1 according to another embodiment, the implant including a plate portion and a mesh portion;

FIG. 7 is a perspective view of the implant illustrated in FIG. 1 according to another embodiment, the implant including a plate portion and a mesh portion;

FIG. 8 is a perspective view of the implant illustrated in FIG. 1 according to another embodiment, the implant including a plate portion and a mesh portion;

FIG. 9 is a perspective view of the implant illustrated in FIG. 1 according to another embodiment, the implant including a plate portion and a mesh portion;

FIG. 10 is an implant according to another embodiment;

FIG. 11 is a perspective view of a bone fixation system according to another aspect of the disclosure, the bone fixation system including an implant and a bone fixation member configured to attach the implant to an underlying fractured bone;

FIG. 12 is a perspective view of the implant illustrated in FIG. 11;

DETAILED DESCRIPTION OF ILLUSTRATIVE EMBODIMENTS

Figure 13:
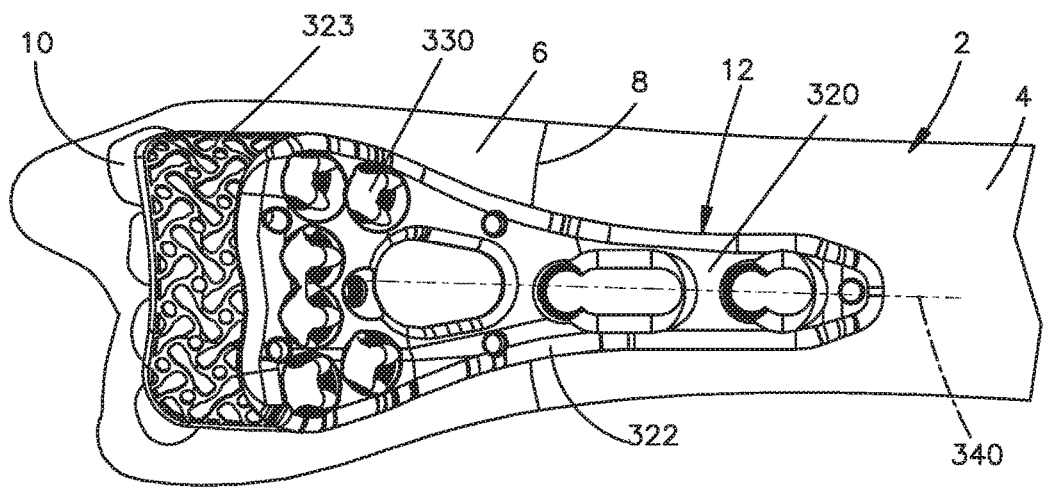
FIG. 13 is a perspective view of a bone fixation system according to another aspect of the disclosure, the bone fixation system including an implant and a bone fixation member configured to attach the implant to an underlying fractured bone.

Certain terminology is used in the following description for convenience only and is not limiting. The words "lower" and "upper" designate directions in the drawings to which reference is made. The words "proximally" and "distally" refer to directions toward and away from, respectively, the surgeon using the medical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure, which are described herein in the context of separate embodiments, may also be provided in combination in a single embodiment. Conversely, various features of the disclosure that are described in the context of a single embodiment may also be provided separately or in any subcombination.

Referring to FIGS. 1 to 2, many typical bone fractures result in a bone having a first bone segment separated from a second bone segment by a defect in the bone, for example the fracture. Sometimes a bone fractures, or splinters into more than two fragments. This type of fracture or splinter of a bone can be referred to as a comminuted fracture. A comminuted fracture of a bone 2 can result in a first bone segment 4, a second bone segment 6 separated from the first bone segment 4 by a defect 6, and at least one additional bone segment 10. The at least one additional bone segment 10 can be much smaller than each of the first bone segment 4 and the second bone segment 6. While an implant can be secured to both the first bone segment 4 and the second bone segment 6, for example through the use of a bone anchor such as a bone screw, the small size of the additional bone segment 10 may discourage the use of a bone anchor being inserted into the additional bone segment 10 to secure the additional bone segment 10 to the implant.

A bone fixation system 12 is configured to be implanted and secured to a bone 2 so as to stabilize a first bone segment 4 of the bone 2 with respect to a second bone segment 6 of the bone 2, the first bone segment 4 separated from the second bone segment 6 by a defect 8. The bone fixation system 12 is further configured to stabilize additional bone segments 10 with respect to the first bone segment 4 and the second bone segment 6. In one example, the bone 2 is a tibia. It should be appreciated, however, that the bone 2 can be any bone in the human or animal anatomy suitable for bone plate fixation. Further, while the bone 2 is illustrated having first and second bone segments 4 and 6, it is appreciated that the bone 2 can include any number of defects or bone segments as desired that are configured for fixation using the bone fixation system 12.

The bone fixation system 12 can include an implant 20 and a plurality of bone anchors 80 that are configured to fix the bone plate 20 to the underlying bone 2, and in particular to each of the first and second bone segments 4 and 6. The bone anchors 80 include a head 82 and a shaft 84 that extends out with respect to the head 82 along a central anchor axis 86. The shaft 84 can extend directly from the head 82, or can extend from a neck that is disposed between the head 82 and the shaft 84. The shaft 84 can be threaded, such that the bone anchor 80 is configured as a bone screw 88 whose shaft 84 extends out relative to the head 82 along the central anchor axis 86, which can also be referred to as a central screw axis. The threaded shaft 84 can be configured to threadedly purchase in the underlying bone 2. For instance, one or more up to all of the bone screw 88 can be configured as a cortical screw whose threaded shaft 84 is designed and configured to threadedly mate to cortical bone. Alternatively or additionally, one or more of the bone screws 88 can be configured as a cancellous screw whose threaded shaft 84 is designed and configured to threadedly mate to cancellous bone. It is appreciated that cancellous bone screws have threads that have a greater pitch than threads of cortical bone screws. Further, the threads of cancellous bone screws typically extend out from the shaft 84 of the bone screw 88 a greater radial distance than the threads of cortical bone screws.

Referring now to FIGS. 1 to 5, the implant 20 includes a plate portion 22 and a mesh portion 23. The plate portion 22 defines a plate body 24. The plate body 24, and thus the plate portion 22, defines an inner plate surface 26 configured to face the underlying bone 2, and an outer plate surface 28 that is opposite the inner plate surface 26. The plate portion 22 further defines a plurality of bone fixation holes 30 that extend through the plate body 24 from the inner plate surface 26 to the outer plate surface 28. The bone fixation holes 30 may include holes configured to receive a permanent fixation device, for example bone screws, nails, etc. The bone fixation holes 30 may further include holes configured to receive a temporary fixation device, for example a K-wire. In particular, the plate body 24, and thus the plate portion 22, includes a plurality of internal surfaces 32 that each extend from the outer plate surface 28 to the inner plate surface 26 and that each define a respective one of the bone fixation holes 30. Each of the bone fixation holes 30 can extend from the outer plate surface 28 to the inner plate surface 26 along a central hole axis 34. The central hole axis 34 can be oriented normal to each of the inner plate surface 26 and the outer plate surface 28. It should be appreciated, of course, that the central hole axis 34 of any of the bone fixation holes 30 can be oriented at an oblique angle with respect to the inner plate surface 26 and outer plate surface 28 as desired.

During a surgical procedure using the bone fixation system 12, the shaft 84 of the bone screw 88 can be inserted through a respective one of the bone fixation holes 30 and into the underlying bone 2. The bone screw 88 can then be rotated, for example about the central anchor axis 86, so as to cause the threaded shaft 84 to be driven into the underlying bone 2 as the threaded shaft 84 threadedly purchases with the underlying bone 2. The threaded shaft 84 can be driven into the underlying bone until the head 82 engages the implant 20.

One or more up to all of the bone screws 88 can be configured as a compression screw whose head 82 is configured to bear against the implant 20 so as to apply a compressive force against the implant 20 toward the underlying bone 2 when the shaft 84 is driven further into the underlying bone 2 after the head 82 has contacted the internal surface 32. The shaft 84 can be driven into the underlying bone a sufficient distance until the desired compressive force has been imparted onto the implant 20. The head 82 of the compression screw is often unthreaded. Similarly, at least a portion up to an entirety of the internal surface 32 can be unthreaded.

In another example, one or more up to all of the bone screw 88 can be configured as locking screws that are configured to lock to the implant 20. In particular, the head 82 can be externally threaded. The internal surface 32 can be similarly threaded so as to be configured to threadedly mate with the threaded head 82. Accordingly, during operation, the shaft 84 can be inserted through the fixation hole 30 and driven into the underlying bone 2 as described above. In particular, when the bone screw 88 is a locking screw, rotation of the screw 88 causes the threaded head 82 to threadedly mate with the internal surface 32. As a result, the screw head 82 fastens the implant 20 to the underlying bone 2 without applying a compressive force onto the implant 20 against the underlying bone 2. The implant 20 can be spaced from the underlying bone 2 when locked to the head 82. Alternatively, the implant 20 can abut the underlying bone 2 when locked to the head 82. At least a portion of the internal surface 32 is typically tapered so as to extend in an axially inward direction, for example toward the central hole axis 34, as the internal surface 32 extends from the outer plate surface 28 toward the inner plate surface 26. Thus, the internal surface 32 is configured to prevent the head 82 from passing completely through the fixation hole 30. The head 82 can define at least one external thread that is circumferentially continuous about the central anchor axis 86. It should be appreciated, however, that the head 82 can be alternatively constructed in any manner desired so as to threadedly mate with the internal surface 32 as described herein.

According to one embodiment, one or more of the fixation holes 38 of the bone plate 30 can be configured as a variable angle locking hole that is configured to threadedly mate with the bone screw 88 at different orientations of the bone screw 88 with respect to the central hole axis 34. That is, when the fixation hole 30 is configured as a variable angle locking hole, the plate body 24, and thus the plate portion 22, includes at least one thread that projects out from the internal surface 32 into the fixation hole 30.

The bone screw 88 can be configured to be inserted into the fixation hole 30 such that the central anchor axis 86 is at one of a plurality of orientations with respect to the central hole axis 34 within a range of orientations at which the threaded head 82 is configured to threadedly mate with the at least one thread in the fixation hole 30. For instance, the bone screw 88 can be configured to be inserted into the fixation hole 30 such that the central anchor axis 86 is at one of a plurality of angles within a range of angles defined by the central anchor axis 86 and the central hole axis 34 at which the threaded head 82 is configured to threadedly mate with the at least one thread in the fixation hole 30. The range of angles can be from approximately zero degrees to approximately fifteen degrees. Thus, the range of angles can define a cone of up to approximately thirty degrees. Thus, it can be said that the at least one thread is configured to threadedly mate with the threaded screw head 82 while the bone screw 88 is inserted into the fixation hole 30 such that the central anchor axis 86 is oriented at a first angle with respect to the central hole axis 34, and the at least one thread is further configured to threadedly mate with the threaded screw head 82 when the bone screw 88 is inserted into the fixation hole 30 such that the central anchor axis 86 is oriented at a second angle with respect to the central hole axis 34 that is different than the first angle. At least one or both of the first and second angles can be non-zero angles. Alternatively, the central anchor axis 86 can be coincident with the central hole axis 34 in one of the orientations in the range of orientations.

According to one aspect of the disclosure, the at least one thread in the fixation hole 30 and the threads of the head 82 are defined prior to insertion of the bone screw 88 into the variable angle locking hole. That is, the internal surface 32 is not designed or configured to cut threads into the bone screw head 82. Similarly, the bone screw head 82 is not designed or configured to cut threads into the internal surface 32. According to another embodiment, the threads of the head 82 are configured to cut threads into the internal surface 32 when the central anchor axis 86 is not coincident with the central hole axis 34.

According to one embodiment, one or more of the fixation holes 38 of the bone plate 30 can be configured as a combination hole that includes a first portion configured to receive a compressive force from a compression screw, and a second portion configured to threadedly mate with a locking screw, a variable angle locking screw, or both. The first portion and the second portion of the combination hole can be open to one another. One or both of the first portion and the second portion may define a substantially circular shape.

The plate body 24, and thus the plate portion 22, can include a shaft portion 36 and a head portion 38. In one example, the shaft portion 36 is configured to overlie a first bone segment, and the head portion 38 is configured to overlie a second bone segment. The shaft portion 36 is elongate along a central shaft axis 40, which may be substantially straight, or may include twists and curvatures to correspond to the shape of a bone to which the implant 20 is to be secured. The head portion 38 is elongate along a central head axis 42, which may be substantially straight, or may include twists and curvatures to correspond to the shape of the bone to which the implant 20 is to be secured. As shown in the illustrated embodiment, the plate portion 22 is configured such that the central shaft axis 40 is angularly offset with respect to the central head axis 42 by about ninety degrees. The plate portion 22 may be configured to correspond to an anterolateral distal tibia.

Each of the shaft portion 36 and the head portion 38 can include at least one up to a plurality of the bone fixation holes 30. The shaft portion 36 may be configured such that the central shaft axis 40 intersects one or more, up to all, of the bone fixation holes 30 in the shaft portion 36. The head portion 38 may be configured such that the central head axis 42 intersects one or more, up to all, of the bone fixation holes 30 in the head portion 38. The plate portion 22 defines an outer plate perimeter 44 that encloses all of the bone fixation holes 30.

As shown in the illustrated embodiment, the plate body 24 defines a side plate surface 46 that extends between the inner plate surface 26 and the outer plate surface 28, for example from the inner plate surface 26 to the outer plate surface 28, such that the side plate surface 46 defines at least a portion of the outer plate perimeter 44 of the plate portion 22. The side plate surface 46 can be described as facing radially outward with respect to the central hole axis 34 of any of the bone fixation holes 30, while the internal surface 32 can be described as facing radially inward with respect to the central hole axis 34 of the bone fixation hole 30 defined by the internal surface 32.

The plate body 24 defines a height H1 measured from the outer plate surface 28 to the inner plate surface 26 along a first direction D1. The first direction D1 can be parallel to the central hole axis 34 of the bone fixation hole 30 that is closest to the location where the height H1 is being measured. The first direction D1 can vary based on the location within the plate body 24 at which the height H1 is being measured, due to twists or curvature of the plate body 24. In one example, the height H1 can be measured at a location 48 that is between two of the bone fixation holes 30, and that intersects the central shaft axis 40. The plate body 24 further defines a length L1 measured along a second direction D2 that can be substantially perpendicular to the first direction D1. In one example, the second direction D2 is substantially parallel to the central shaft axis 40. The plate body 24 further defines a width W1 measured along a third direction D3 that can be substantially perpendicular to both the first direction D1 and the second direction D2. In one example, the third direction D3 is substantially parallel to the central head axis 42. As shown in the illustrated embodiment, the plate portion 22 can be configured such that the plate body 24 defines a maximum value for the length L1, a maximum value for the width W1, and a maximum value for the height H1, wherein the maximum value for the length L1 is greater than the maximum value for the width W1, and the maximum value for the width W1 is greater than maximum value for the height H1.

The plate portion 22 may be configured to resist bending by hand. According to one embodiment, the plate portion 22 defines a stiffness that is sufficient to prevent changing the shape of the plate portion 22 by hand. The plate portion 22 may further be configured to define a stiffness that allows the shape of the plate portion 22 to be changed with the use of tools, but prevents changing the shape of the plate portion 22 by hand.

The mesh portion 23 defines a mesh body 25. The mesh portion 23 is configured to cradle, or support, the additional bone segment(s) 10 without the use of bone fixation elements (such as bone screws) being inserted into each of the additional bone segments 10. The mesh body 25, and thus the mesh portion 23, defines an inner mesh surface 27 configured to face an underlying bone, and an outer mesh surface 29 that is opposite the inner mesh surface 27. In one example, the mesh portion 23 can define at least one aperture 31, such as a plurality of apertures 31, which extends through the mesh body 25 from the outer mesh surface 27 to the inner mesh surface 29.

The apertures 31 can include a plurality of inner apertures 33 that extend through the mesh body 25 along a fourth direction D4 from the outer mesh surface 27 to the inner mesh surface 29. The apertures 31, according to one embodiment, are smaller than the bone fixation holes 30 of the plate portion 22. According to one embodiment, the apertures 31 are sized such that the apertures 31 are too small to receive a K-wire. Thus, the apertures 31 are not configured to receive one of the bone anchors 80 that the bone fixation hole 30 are configured to receive. According to one embodiment, the apertures 31 are not configured to receive any bone anchors. According to another embodiment, the apertures 31 are configured to receive a bone anchor that is much smaller than the bone anchor 80, for example a bone anchor that is smaller in diameter than a K-wire.

The mesh portion 23 may include a mesh outer perimeter 35 defined by the mesh body 25. According to one embodiment, the mesh body 25 includes a side mesh surface 37 that extends between the inner mesh surface 27 and the outer mesh surface 29 such that the side mesh surface 37 defines at least a portion of the mesh outer perimeter 25. At least some up to all of the inner apertures 33 can be fully enclosed about their respective perimeters by the mesh body 25, for example the side mesh surface 37.

The apertures 31 can combine so as to define linkages 39. The linkages 39 can be interconnected, elastic, flexible, or any combination thereof. Further, the linkages 39 can be monolithic with each other. The linkages 39 in combination with the apertures 31 are configured to abut multiple, small bone segments and retain the segments in place while the bone heals resulting in reconnection of the multiple, small bone segments.

The mesh portion 23 can be configured to be flexible, resilient, or both. The linkages 39 and apertures 31 can combine to define an elastically flexible region of the mesh body 25. The mesh portion 23 can include as many or as few apertures 31 as desired.

The mesh body 25 defines a height H2 measured from the outer mesh surface 29 to the inner mesh surface 27 along the fourth direction D4. The height H2 can be measured at a location 41 within the mesh portion 23, for example on one of the linkages 39. The fourth direction D4 can be parallel to first direction D1, or alternatively, can be oblique to the first direction D1. The fourth direction D4 can be normal to the outer mesh surface 29 at the location at which the depth D4 is being measured.

The mesh body 25 further defines a length L2 measured along a fifth direction D5 that can be substantially perpendicular to the fourth direction D4. In one example, the fourth direction D4 is substantially parallel to the second direction D2. The mesh body 25 further defines a width W2 measured along a sixth direction D6 that can be substantially perpendicular to both the fourth direction D4 and the fifth direction D5. In one example, the sixth direction D6 is substantially parallel to the third direction D3. As shown in the illustrated embodiment, the mesh portion 23 can be configured such that the mesh body 25 defines a maximum value for the length L2, a maximum value for the width W2, and a maximum value for the height H2, wherein the maximum value for the height H2 is less than each of the maximum value for the length L1 and the maximum value for the width W1. As shown in the illustrated embodiment, the maximum value for the height H2 of the mesh portion 23 can be less than the maximum value for the height H1 of the plate portion 22. According to one aspect of the disclosure, the maximum value for the height H2 of the mesh portion 23 may be between about 0.25 and about 1.0 mm, and the maximum value for the height H1 of the plate portion 22 may be between about 1.25 mm to about 4.5 mm. According to one aspect of the disclosure, the implant 20 defines a ratio of the maximum value for the height H1 of the plate portion 22 to the maximum value for the height H2 of the mesh portion 23 of about 5:1.

The mesh portion 23 can be configured to be less stiff than the plate portion 22. For example, the mesh portion 23 can be configured to be bent by hand, while the plate portion 22 can be configured to resist bending by hand.

The implant 20 includes the plate portion 22 and the mesh portion 23, the mesh portion attached to the plate portion 22.

The mesh portion 23 can extend from the plate portion 22. As shown in the illustrated embodiment, the mesh portion 23 extends from a portion of the plate portion 22 such that the implant 20 defines an outer implant perimeter 50 that is defined partially by the plate portion 22 and partially by the mesh portion 23. For example, the outer implant perimeter 50 may be partially defined by the outer plate perimeter 44 and partially by the outer mesh perimeter 35.

The plate portion 22 may be monolithic with the mesh portion 23 such that the plate portion 22 and the mesh portion 23 form a single member, and cannot be separated without plastically deforming the implant 20. The mesh portion 23 may extend from a portion, less than the entirety, of the side plate surface 46. According to one embodiment, the mesh portion 23 extends only from the head portion 38 of the plate portion 22. The maximum value of the width W2 of the mesh portion 23 may be equal to or less than the maximum value of the width W1 of the plate portion 22, the maximum value of the length L2 of the mesh portion 23 may be less than the maximum value of the length L1 of the plate portion 22, the maximum value of the height H2 of the mesh portion 23 may be less than the maximum value of the height H1 of the plate portion 22, or any combination thereof.

Referring to FIG. 6, according to one embodiment the apertures 31 can include at least one outer aperture 43, which is defined by the side mesh surface 37 and open to an exterior of the implant 20. The at least one outer aperture 43 of the apertures 31 can include a plurality of outer apertures 43. In one example, each of the outer apertures 43 can be configured as a slot that that extends into the mesh body 25 toward the plate portion 22. The outer apertures 43 can be spaced from each other, for example along the sixth direction D6. The outer apertures 43 can be equidistantly spaced from each other, or alternatively, the outer apertures 43 can be spaced from each other at different distances.

Thus, the outer apertures 43 can divide the mesh body 25 into a plurality of petals 45 that extend in a direction, for example the second direction D2, the fifth direction D5, or both. Each one of the petals 45 can be moved independently of the other petals 45. As shown in the illustrated embodiment, the plurality of petals 45 can define a continuous body, for example such that each of the petals 45 extends from a common base portion 47 of the mesh body 25. The base portion 47 can be attached directly to the plate portion 22. Alternatively, one or more of the petals 45 may be separate from one another such that each of the petals 45 extends from a separate portion of the plate body 24.

Referring to FIGS. 7 to 9, the mesh portion 23 can include one or more bone fixation holes 49 configured to receive a bone anchor, for example a bone anchor configured to be received by the bone fixation hole 30, to secure the mesh portion 23 to an underlying bone segment. The bone fixation hole 49 can be surrounded by a combination of the linkages 39 and the apertures 31, for example the inner apertures 33. According to one aspect of the disclosure, the mesh portion 23 may be configured such that the linkages 39 are flexible to allow the mesh portion 23 to be contoured to match an underlying bone without altering the integrity of the bone fixation hole 49 such that the bone fixation hole 49 is able to receive a bone fixation element to secure the implant 20 to the bone 2. Thus, the mesh portion 23 may include the linkages 39 that are contourable and the bone fixation hole 49 that is configured to receive a bone fixation element to secure the implant 20 to the bone 2 before and after the linkages 39 have been contoured.

The petals 45 can each include zero, one, or a plurality of the bone fixation holes 49. In one example, each of the petals 45 can include the same number of the bone fixation holes 49. Alternatively, different ones of the petals 45 can include a different number of the bone fixation holes 49. As shown in FIG. 8, the bone fixation holes 49 may be connected to the plate portion 22 by an arm 51 and separated from surrounding linkages 39. The arm 51 may have a width greater than that of the linkages 39 in the mesh portion 23. As shown in FIG. 9, the bone fixation holes 49 may be connected directly to one or more of the linkages 39.

Two or more of the bone fixation holes 49 can be aligned with respect to one or more of the second direction D2, the third direction D3, the fifth direction D5, and the sixth direction D6. As shown in the embodiment illustrated in FIG. 8, the mesh portion 23 includes a first bone fixation hole 49a and a second bone fixation hole 49b that are aligned with respect to the third direction D3, and the sixth direction D6. As shown in the embodiment illustrated in FIG. 9, the mesh portion 23 includes the first bone fixation hole 49a, the second bone fixation hole 49b, a third bone fixation hole 49c, and a fourth bone fixation hole 49d. The first bone fixation hole 49a and the second bone fixation hole 49b are aligned with respect to the third direction D3, and the sixth direction D6, the third bone fixation hole 49c and the fourth bone fixation hole 49d are aligned with respect to the third direction D3, and the sixth direction D6, the first bone fixation hole 49a and the third bone fixation hole 49b are aligned with respect to the second direction D2, and the fifth direction D5, and the second bone fixation hole 49b and the fourth bone fixation hole 49d are aligned with respect to the second direction D2, and the fifth direction D5. It will be appreciated that other numbers and arrangements of the bone fixation holes 49 can be provided.

Referring to FIG. 10, the bone fixation system 12 may include an implant 120 configured to be secured to a calcaneus bone to repair a defect in the calcaneus bone. The implant 120 includes a number of features similar to those described above in reference to FIGS. 1 to 9 such that the description of FIGS. 1 to 9 applies to the embodiment illustrated in FIG. 10, except where differences are highlighted below. Similar elements in FIGS. 1 to 9 and FIG. 10 are identified with reference numbers increased by 100. Thus, for example, the description of the bone fixation holes 30 also applies to bone fixation holes 130 as described herein.

The implant 120 includes a plate portion 122 and a plurality of mesh portions 123. The plate portion 122 includes a plate body 124 that defines a serpentine shape. The plate portion 122 includes a plurality of bone fixation holes 130 arranged along the serpentine shape. The plate body 124 may include one or more extensions 152 from the serpentine shape. The extensions 152 can include another of the bone fixation holes 130.

The plurality of mesh portion 123 extend from spaced locations of the plate portion 122, such that the plurality of mesh portions 123 are spaced from each other by portions of the plate portion 122. As shown in the illustrated embodiment, a first mesh portion 123a is spaced from a second mesh portion 123b by a first extension 152a of the plate portion 122. The implant 120 can further include a third mesh portion 123c spaced from the second mesh portion 123b by a second extension 152b of the plate portion 122. The second extension 152b is spaced from the first extension 152a by the second mesh portion 123b. Thus, the implant 120 defines an outer implant perimeter 150 defined by alternating portions of the plate 122 and mesh portions 123. As shown the outer implant perimeter 150, starting at a location 154 and going counter-clockwise, is defined by the plate portion 122, the first mesh portion 123a, the plate portion 122, the second mesh portion 123b, the plate portion 122, and the third mesh portion 123c, and the plate portion 122.

The implant 120 can include one or more tabs 154 configured to be bent to correspond to a shape of an underlying bone. The tabs 154 can be devoid of bone fixation holes 130. The plate portion 122, one or more of the mesh portions 123, or both can include one or more of the tabs 154.

Referring to FIGS. 11 and 12, the bone fixation system 12 may include an implant 220 configured to be secured to a tibia bone to repair a distal tibia pilon fracture. The implant 220 includes a number of features similar to those described above in reference to FIGS. 1 to 9 such that the description of FIGS. 1 to 9 applies to the embodiments illustrated in FIGS. 11 and 12, except where differences are highlighted below. Similar elements in FIGS. 1 to 9 and FIGS. 11 to 12 are identified with reference numbers increased by 200. Thus, for example, the description of the bone fixation holes 30 also applies to bone fixation holes 230 as described herein.

The implant 220 includes a plate portion 222 and a mesh portion 223. The plate portion 222 includes a plate body 224, the plate body 224 including a shaft portion 236 and a head portion 238. In one example, the shaft portion 236 is configured to overlie a first bone segment, and the head portion 238 is configured to overlie a second bone segment. The shaft portion 236 is elongate along a central shaft axis 240, which may be substantially straight, or may include twists and curvatures to correspond to the shape of a bone to which the implant 220 is to be secured. The head portion 238 is elongate along a central head axis 242, which may be substantially straight, or may include twists and curvatures to correspond to the shape of the bone 2 to which the implant 220 is to be secured. As shown in the illustrated embodiment, the plate portion 222 is configured such that the central shaft axis 240 is angularly offset with respect to the central head axis 242 by about ninety degrees.

The mesh portion 223 extends from the head portion 238 in a plurality of directions. As shown in the illustrated embodiment, the head portion 238 can be surrounded by mesh portion 223 except for where the shaft portion 236 joins to the head portion 238. The mesh portion 223 can extend from the head portion 238 in both directions that make up a lateral direction A, for example the mesh portion 223 can extend out from one portion 260 of a side plate surface 246, and can further extend out from another portion 262 of the side plate surface 246 that is opposite the one portion 260 with respect to the lateral direction A. The mesh portion 223 can extend from the head portion 238 in both directions that make up a longitudinal direction L, for example the mesh portion 223 can extend out from one portion 264 of the side plate surface 246, and can further extend out from another portion 266 of the side plate surface 246 that is opposite the one portion 264 with respect to the longitudinal direction L. The mesh portion 223 can define a maximum dimension, for example a maximum width W2 greater than a maximum width W1 of the plate portion 222. As shown the maximum width W2 and the maximum width W1 can be measured along the lateral direction A. The mesh portion 223 may be configured to be cut, such that sections of the mesh portion 223 may be removed to allow the remaining portion of the mesh portion 223 to have an improved fit with the underlying bone.

Figure 14:
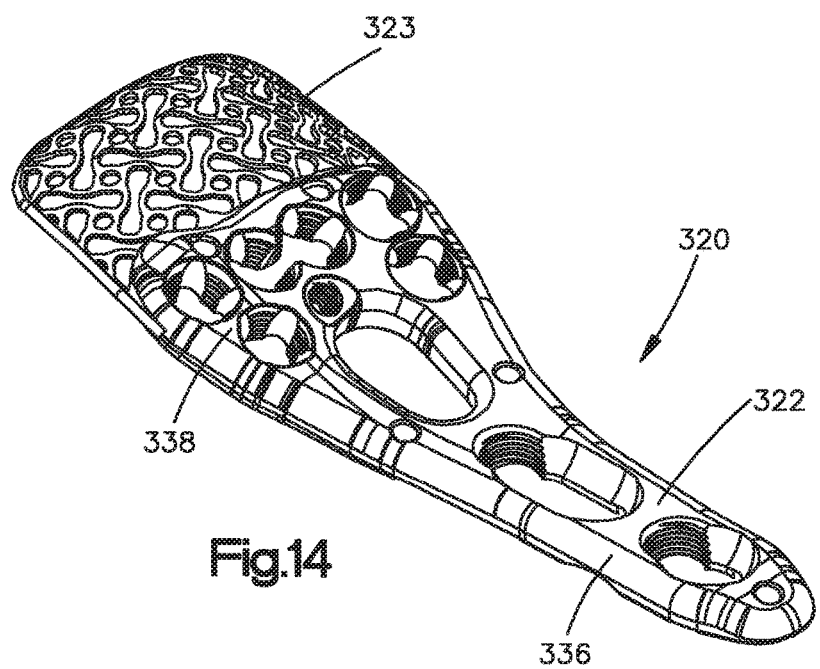
FIG. 14 is a perspective view of the implant illustrated in FIG. 13.

Referring to FIGS. 13 and 14 the bone fixation system 12 may include an implant 320 configured to be secured to a radius bone to repair a distal radius fracture. The implant 320 includes a number of features similar to those described above in reference to FIGS. 1 to 9 such that the description of FIGS. 1 to 9 applies to the embodiments illustrated in FIGS. 13 and 14, except where differences are highlighted below. Similar elements in FIGS. 1 to 9 and FIGS. 13 to 14 are identified with reference numbers increased by 300. Thus, for example, the description of the bone fixation holes 30 also applies to bone fixation holes 330.

The implant 320 includes a plate portion 322 and a mesh portion 323. The plate portion 322 includes a plate body 324, the plate body 324 including a shaft portion 336 and a head portion 338. In one example, the shaft portion 336 is configured to overlie a first bone segment, and the head portion 338 is configured to overlie a second bone segment. The shaft portion 336 is elongate along a central shaft axis 340, which may be substantially straight, or may include twists and curvatures to correspond to the shape of a bone to which the implant 320 is to be secured. The head portion 338 is generally aligned with the shaft portion 336, and the head portion 338 is enlarged, or wider than the shaft portion 336 to accommodate a plurality of bone fixation holes 330. The mesh portion 323 extends from the plate portion 322, for example, the head portion 338 in a direction substantially parallel to the central shaft axis 340.

Referring to FIGS. 1 to 14, a method of use of the bone fixation system 12 is described below. Reference is made to the implant 20, the plate portion 22, and the mesh portion 23 but it will be understood that the steps below may also be performed with any of the implants 120, 220, and 320. A method of stabilizing a fractured bone 2 may include the step of selecting an implant 20 including a plate portion 22 and a mesh portion 23, the plate portion 22 configured to be secured to both a first bone segment 4 of the bone 2, a second bone segment 6 of the bone 2 that is separated from the first bone segment 4 by a defect 8 in the bone 2, and the mesh portion 23 configured to abut at least one additional segment 10 of the bone 2.

The method can include the step of positioning the implant 20 adjacent the bone 2 such that a shaft portion 36 of the plate portion 22 faces the first bone segment 4 and a head portion 38 of the plate portion 22 faces the second bone segment 6. The positioning step can further include the step of abutting the mesh portion 23 with the at least one additional segment 10 of the bone 2. The shaft portion 36 includes a first bone fixation hole 30 and the head portion 38 includes a second bone fixation hole 30. The method can include the steps of inserting a first bone anchor 80 through the first bone fixation hole 30 and into the first bone segment 4, and inserting a second bone anchor 80 through the second bone fixation hole 30 and into the second bone segment 6.

According to one embodiment, the method does not include the step of inserting a bone anchor through the mesh portion 23, for example through an aperture 31 of the mesh portion 23.

LIST OF EXAMPLES

A non-exhaustive list of examples of the bone fixation system 12, the implants 20, 120, 220, and 320, and methods of use of the bone fixation system 12 and the implants 20, 120, 220, and 320 described above is provided below.

Example 1

An implant configured to be secured to a bone, the implant comprising: a plate portion; and an implant portion, wherein the implant defines an outer perimeter defined by at least partially by the plate portion and further defined at least partially by the mesh portion.

Example 2

The implant of example 1, wherein the plate portion includes a plate body that defines an inner plate surface and an outer plate surface, the inner plate surface configured to face the bone, the outer plate surface opposite the inner plate surface.

Example 3

The implant of example 2, wherein the inner plate surface is spaced from the outer plate surface with respect to a first direction, and the plate portion defines a plate height measured from the inner plate surface to the outer plate surface along the first direction.

Example 4

The implant of example 3, wherein the mesh portion includes a mesh body that defines an inner mesh surface and an outer mesh surface, the inner mesh surface configured to face the bone, the outer mesh surface opposite the inner mesh surface.

Example 5

The implant of example 4, wherein the inner mesh surface is spaced from the outer mesh surface with respect to a second direction, the mesh portion defines a mesh height measured from the inner mesh surface to the outer mesh surface along the second direction, and the mesh height is less than the plate height.

Example 6

The implant of example 5, wherein the first direction is parallel to the second direction.

Example 7

The implant of example 5, wherein the first direction is non-parallel to the second direction.

Example 8

The implant of any one of examples 5 to 7, wherein the plate portion includes a bone fixation hole that extends through the plate body between the inner plate surface and the outer plate surface, and the bone fixation hole is configured to receive a bone anchor to secure the implant to the bone.

Example 9

The implant of example 8 wherein plate body defines a central hole axis, and the bone fixation hole extends along the central hole axis between the inner plate surface and the outer plate surface.

Example 10

The implant of example 9, wherein the central hole axis is parallel to the first direction.

Example 11

The implant of any one of example 8 to 10, wherein the bone fixation hole is a first bone fixation hole, the plate portion includes a second bone fixation hole that extends through the plate body between the inner plate surface and the outer plate surface.

Example 12

The implant of example 11, wherein the plate height is measured at a location between the first bone fixation hole and the second bone fixation hole.

Example 13

The implant of example 12, wherein the plate body defines a side plate surface that extends between the inner plate surface and the outer plate surface such that the side plate surface, and the side plate surface defines an outer plate perimeter that encloses all of the bone fixation holes of the implant that are configured to receive a bone anchor configured to secure the implant to the bone.

Example 14

The implant of example 13, wherein the mesh portion extends out from a portion of the side plate surface.

Example 15

The implant of any one of examples 13 to 14, wherein the mesh portion defines an aperture that extends through the mesh body between the inner mesh surface and the outer mesh surface.

Example 16

The implant of example 15, wherein the aperture is smaller than all of the bone fixation holes of the implant such that the aperture is not configured to receive the bone anchor.

Example 17

The implant of example 16, wherein the mesh portion defines a plurality of apertures, the mesh body includes a side mesh surface that extends between the inner mesh surface and the outer mesh surface, and the side mesh surface defines an outer mesh perimeter that encloses the plurality of apertures.

Example 18

The implant of example 17, wherein the plurality of apertures includes an inner aperture and an outer aperture, the inner aperture including a fully enclosed perimeter defined by the mesh body, and the outer aperture extends into the mesh body toward the plate portion.

Example 19

The implant of example 18, wherein the mesh portion includes a first petal and a second petal, the first petal separated from the second petal by the outer aperture such that the first petal is independently flexible relative to the second petal.

Example 20

The implant of any one of examples 1 to 19, wherein the mesh portion is a first mesh portion, the implant includes a second mesh portion separated from the first mesh portion by the plate portion.

Example 21

The implant of example 20, wherein the implant includes a third mesh portion separated from the second mesh portion by the plate portion.

Example 22

The implant of any one of examples 1 to 21, wherein the mesh portion is more flexible than the plate portion.

Example 23

The implant of any one of example 1 to 22, wherein the plate portion is configured to be secured to a first segment of a tibia by a first bone anchor, the plate portion is configured to be secured to a second segment of the tibia by a second bone anchor, and the mesh portion is configured to abut a third segment of the tibia.

Example 23

The implant of any one of example 1 to 22, wherein the plate portion is configured to be secured to a first segment of a calcaneus by a first bone anchor, the plate portion is configured to be secured to a second segment of the calcaneus by a second bone anchor, and the mesh portion is configured to abut a third segment of the calcaneus.

Example 23

The implant of any one of example 1 to 22, wherein the plate portion is configured to be secured to a first segment of a radius by a first bone anchor, the plate portion is configured to be secured to a second segment of the radius by a second bone anchor, and the mesh portion is configured to abut a third segment of the radius.

Example 24

A kit comprising: the implant of any one of claims 1 to 23; and a plurality of bone anchors configured to secure the implant to the bone.

Example 25

The kit of example 24, wherein the plurality of bone anchors includes a plurality of bone screws.

Example 26

The kit of example 25, wherein the plurality of bone screws includes compression screws, locking screws, variable angle locking screws, and any combination thereof.

Each of these non-limiting examples can stand on its own, or can be combined in various permutations or combinations with one or more of the other examples.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An implant comprising:
    a plate portion; and
    a mesh portion that extends from the plate portion,
        wherein the implant defines an outer perimeter defined at least partially by the plate portion and further defined at least partially by the mesh portion;
        wherein the mesh portion is a first mesh portion and the implant includes a second mesh portion separated from the first mesh portion by the plate portion.

2. The implant of claim 1, wherein the plate portion includes a plate body that defines an inner plate surface and an outer plate surface, the inner plate surface configured to face the bone, the outer plate surface opposite the inner plate surface.

3. The implant of claim 2, wherein the inner plate surface is spaced from the outer plate surface with respect to a first direction, and the plate portion defines a plate height measured from the inner plate surface to the outer plate surface along the first direction.

4. The implant of claim 3, wherein the mesh portion includes a mesh body that defines an inner mesh surface and an outer mesh surface, the inner mesh surface configured to face the bone, the outer mesh surface opposite the inner mesh surface.

5. The implant of claim 4, wherein the inner mesh surface is spaced from the outer mesh surface with respect to a second direction, the mesh portion defines a mesh height measured from the inner mesh surface to the outer mesh surface along the second direction, and the mesh height is less than the plate height.

6. The implant of claim 5, wherein the first direction is parallel to the second direction.

7. The implant of claim 5, wherein the plate portion includes a bone fixation hole that extends through the plate body between the inner plate surface and the outer plate surface, and the bone fixation hole is configured to receive a bone anchor to secure the implant to the bone.

8. The implant of claim 7 wherein plate body defines a central hole axis, and the bone fixation hole extends along the central hole axis between the inner plate surface and the outer plate surface.

9. The implant of claim 8, wherein the central hole axis is parallel to the first direction.

10. The implant of claim 7, wherein the bone fixation hole is a first bone fixation hole, the plate portion includes a second bone fixation hole that extends through the plate body between the inner plate surface and the outer plate surface.

11. The implant of claim 10, wherein the plate height is measured at a location between the first bone fixation hole and the second bone fixation hole.

12. The implant of claim 11, wherein the plate body defines a side plate surface that extends between the inner plate surface and the outer plate surface such that the side plate surface defines an outer plate perimeter that surrounds all of the bone fixation holes of the implant that are configured to receive a bone anchor configured to secure the implant to the bone.

13. The implant of claim 12, wherein the mesh portion extends out from a portion of the side plate surface.

14. The implant of claim 12, wherein the mesh portion defines an aperture that extends through the mesh body between the inner mesh surface and the outer mesh surface, and the aperture is smaller than all of the bone fixation holes of the implant such that the aperture is not configured to receive the bone anchor.

15. The implant of claim 14, wherein the mesh portion defines a plurality of apertures, the mesh body includes a side mesh surface that extends between the inner mesh surface and the outer mesh surface, and the side mesh surface defines an outer mesh perimeter that encloses the plurality of apertures.

16. The implant of claim 15, wherein the outer perimeter of the implant is defined by the outer plate perimeter and the outer mesh perimeter.

17. The implant of claim 15, wherein the plurality of apertures includes an inner aperture and an outer aperture, the inner aperture including a fully enclosed perimeter defined by the mesh body, and the outer aperture extends into the mesh body toward the plate portion.

18. The implant of claim 17, wherein the mesh portion includes a first petal and a second petal, the first petal separated from the second petal by the outer aperture such that the first petal is independently flexible relative to the second petal.

19. A method of stabilizing a bone, the bone including a first bone fragment, a second bone fragment, a third bone fragment, a first defect between the first bone fragment and the second bone fragment, and a second defect between the second bone fragment and the third bone fragment, the method comprising the steps of:
   moving an implant toward the bone, the implant including a plate portion, a mesh portion, and an outer perimeter defined in part by the plate portion and in part by the mesh portion, wherein the mesh portion is a first mesh portion and the implant includes a second mesh portion separated from the first mesh portion by the plate portion;
   inserting a bone anchor through a first bone fixation hole defined by the plate portion, and into the first bone segment;
   inserting a second bone anchor through a second bone fixation hole defined by the plate portion, and into the second bone segment; and
   abutting the mesh portion with the third bone segment.

\* \* \* \* \*